# United States Patent [19]

Benner

[11] Patent Number: 5,958,702
[45] Date of Patent: Sep. 28, 1999

[54] RECEPTOR-ASSISTED COMBINATORIAL CHEMISTRY

[76] Inventor: Steven Albert Benner, 525 S. Catalina, Pasadena, Calif. 91106

[21] Appl. No.: 08/386,521

[22] Filed: Feb. 6, 1995

[51] Int. Cl.[6] .......................... G01N 33/53; A61K 38/00
[52] U.S. Cl. ............................... 435/7.1; 530/339
[58] Field of Search .................. 435/7.1; 558/286; 530/339

[56] References Cited

U.S. PATENT DOCUMENTS 5,366,862  11/1994  Venton et al. .......................... 435/7.1

Primary Examiner—Keith D. MacMillan
Assistant Examiner—Joseph W. Ricigliano

[57] ABSTRACT

This invention provides a method for preparing molecules that bind to a preselected receptor, whereby the receptor itself acts as an agent for either joining two ligand fragments to form a composite, tight binding ligand, or selects a composite ligand from a mixture in solution where ligand fragments are being joined and unjoined reversibly under equilibrium conditions.

5 Claims, No Drawings

RECEPTOR-ASSISTED COMBINATORIAL CHEMISTRY

CROSS REFERENCES TO RELATED APPLICATIONS

None

STATEMENT OF RIGHTS TO INVENTIONS MADE UNDER FEDERALLY-SPONSORED RESEARCH

None

BACKGROUND OF THE INVENTION

1. Field of the Invention

This invention relates to the fields of molecular diversity and combinatorial chemistry, which includes general strategies for obtaining ligands that bind to a preselected receptor starting from a collection, or library, of compounds presented to the receptor as a mixture. This invention relates to a method for increasing the power of combinatorial strategies by increasing the number of compounds that can be explored in a combinatorial experiment. This invention provides a method for preparing molecules (ligands) that bind to a preselected receptor, where the receptor extracts two or more ligand fragments, and where the ligand fragments are joined covalently while bound to the receptor. More specifically, it describes a method whereby a biological receptor is presented with a mixture, or library, of compounds that represent widely different types of structures, where each of these compounds bears one or more reactive groups that can form a covalent bond by reaction with a reactive group from another compound in the library, where two or more compounds in the library are joined either while bound to the receptor itself, or in solution, where the composite ligand is then trapped by the receptor. The product of the receptor-assisted synthesis is isolated as a complex with the receptor, and then released and analyzed.

2. Description of the Related Art

Background

The majority of pharmaceutical agents are compounds that exert their biological activity by binding to a biological macromolecule, referred to here as a receptor. The discovery of ligands that can bind to a preselected receptor and thereby exert a biological effect is therefore a central task of medicinal chemists seeking to develop new human pharmaceutical agents.

Classically, ligands are discovered by three strategies. The first involves screening of a collection of chemicals whose structures have no deliberate connection with the structure or biology of the target receptor. This process is referred to as "random screening".

The second strategy requires information about the structure of the natural ligand for a receptor. Development of new ligands then is based on the deliberate synthesis of specific analogs of the natural ligand in the hope of discovering a ligand that retains or has increased affinity for the receptor, together with bioavailability, stability, and other properties desired for a human pharmaceutical.

The third strategy requires information about the structure of the receptor itself, obtained by crystallography, spectroscopy, or modeling. With this information, ligands are designed by the design of structures that are complementary to the binding site of the ligand.

The deficiencies of these three approaches are well known by those familiar with the art. Random input screening often requires examination of tens of thousands of compounds before a single ligand has a chance of being identified. Analogs of the natural ligands often resemble the natural ligand in terms of bioavailability, stability, or other properties; often, these properties are undesirable in a human pharmaceutical. Further, while tremendous strides have been made in the science of molecular recognition over the past decade, it is still not possible to design a ligand for a receptor, even given a high resolution experimental structure for the receptor itself.

The difficulties in screening can be illustrated by the enormous number of compounds that are possible. For example, a single small molecule built from only carbon and hydrogen with a molecular mass of 282 and the molecular formula $C_{20}H_{42}$ can occur in 366,319 distinct isomers. Adding a single oxygen to this molecule to yield the molecular formula $C_{20}H_{42}O$ increases the number of possible compounds to over $10^7$. The number of possible molecules rapidly becomes astronomical as still more atom types are introduced, or as different ratios of atom types are permitted, or as larger molecules are considered. In principle, each of these might have a distinct affinity for a biological receptor.

One possible method to circumvent these problems comes under the title of "combinatorial chemistry". In a combinatorial experiment, a collection, or library, of molecules with diverse structures is presented to the receptor. The receptor binds to only a few molecules in the library. The binding is then used to extract from the mixture those molecules that bind, or to otherwise identify those molecules that bind, and the structures of the molecules are determined.

The execution of a combinatorial experiment requires the design of several interacting elements. The library must be designed, including both its degeneracy (how many different compounds are in the library) and its diversity (the range of different types of structures that a library contains). Methods must be designed to analyze the structure of the compound that binds to the receptor.

The decisions to chose a particular library diversity and library degeneracy depend, however, on an estimate of the probability that a library with a specified diversity and degeneracy will contain at least one compound that binds as a ligand to a preselected receptor with an affinity sufficient that the ligand can be detected by a receptor binding assay. Likewise, assessing the utility of a combinatorial tool depends on this estimate.

(a) Estimating the Degeneracy of a Useful Library

We now estimate the degeneracy of a library needed to provide useful ligands. To be useful, a library in general must contain at least one compound that binds to the preselected receptor with a disassociation constant of ca. 1 micromolar ($\mu M$) or less. Assuming that the library samples structural diversity randomly, we ask how big the library must be to contain at least one ligand that binds with this affinity. This question is difficult to answer analytically. However, a biological analog to the combinatorial chemistry can be found in the immune system, which has evolved over several hundred million years to solve the complementary problem: to provide a library of receptors that contains at least one that binds to the general ligand with ca. 1 micromolar affinity. The immune system creates a combinatorial pool of receptors (antibodies) that has a high probability of including at least one that binds to any particular ligand. Thus, the immune system solves a problem that is in many respects the reciprocal of the problem that must be solved in a combinatorial experiment.

If we assume that the task of generating combinatorial pool of receptors to find one that binds tightly to a single ligand, and the task of generating a combinatorial pool of ligands to find one that binds tightly to a single receptor, are governed by similar statistics, we may use the statistics of the primary immune response to estimate the degeneracy that a combinatorial library must have to containing a ligand with this affinity. The immune system has $10^7$ to $10^8$ mature B cells. When challenged for the first time with a ligand (the antigen), this repertoire contains some antibodies that bind the antigen with disassociation constants in the range of 100 nM to 10 $\mu$M. This is the "primary response" of the immune system. This suggests that a combinatorial library of $10^8$ molecules is needed if one is to have a good chance of finding a ligand with a disassociation constant on the order of 1 $\mu$M within that library. This suggests that for a combinatorial library of small molecules to be useful, it must have this degeneracy.

The diversity of the library generated by the immune system is also defined. Antibodies are built from 20 natural amino acids containing a specific, and limited, range of functional groups (hydroxyl groups, amino groups, carboxyl groups, amide groups, and four types of aromatic groups). This suggests that for a combinatorial library of small molecules to be useful, it must have a similar range of functional group diversity.

(b) Designing the Receptor Binding Assay

Once a library of $10^8$ degeneracy is chosen, certain constraints are placed on the design of a receptor binding assay. A typical receptor binding assay can conveniently recover a ligand only when either the concentration of the ligand or the concentration of the receptor is at or greater than the disassociation constant of the ligand-receptor complex. Further, a receptor binding assay must be based on the receptor-ligand interaction changing the behavior of either the receptor or the ligand in a way that is detectable. The choice of which component of a receptor binding assay to have in excess is determined in part by what detection system will be used to detect a ligand. Finally, the receptor-binding assay must in some way produce either enough ligand or enough of an associated tag to permit subsequent chemical analysis to determine the structure of the high affinity ligand.

If $10^8$ ligands must be present to have at least one with a disassociation constant ($K_d$) of $10^{-6}$ M, the total concentration of a ligand pool, the sum of the concentrations of each of the components in a library, free in solution must be 100 M for the single compound that is a ligand to be at a concentration equal to the disassociation constant. This is, of course, not possible in any general way (pure water has a concentration of only 55 M).

Thus, the total concentration of the library is roughly inversely proportional to the average molecular weight of the components of the library, and is limited by the solubility of the library components. For an average mass of 200 daltons, a maximum concentration (representing a situation whether the compounds in the library constitute 100% of the solution) is 5 molar. A total library concentration greater than ca. 1 molar will only in exceptional cases be feasibly presented in solution to a receptor; the maximum feasible total concentration of the average library is more likely to be ca. 100 mM.

These facts make difficult the presentation of a useful library to a receptor in soluble form, where the library components saturate the receptor. In order to have the appropriate diversity, the library must contain $10^8$ molecules. Yet the practical total concentration of the library cannot be higher than 1M (more preferably 100 mM). Thus, the concentration of each component in the library can be only 10 nM (more preferably 1 nM). This concentration is well below the disassociation constant of the most tightly bound ligand likely to be found in a library of this size.

One might, of course, immobilize a receptor on an affinity support and pass the library through a column of the support. Compounds that are ligands will be retarded as they pass through the column, as in a standard affinity chromatography experiment, with the degree of retardation depending on the effective concentration of the receptor. However, to separate the forward running ligand from the lagging non-ligands in the column, either the ligand pool must be highly concentrated, or the column must have large dimensions.

It is possible to present the library in soluble form and the receptor in concentrations higher than the disassociation constant. Under these circumstances, all of the most tightly bound ligand will be recovered with the receptor. However, the amount recovered will be limited by the amount of the ligand in the volume used in the combinatorial experiment. This volume can, of course, be made arbitrarily large. However, this requires arbitrarily large amounts of receptor.

Calculations of this sort have convinced many skilled in the art that the only practical implementation of the combinatorial strategy requires that the library of ligands of random structure be presented to the receptor in immobilized form, either on a surface or on small beads, each bearing multiple copies of a single compound in the library. The receptor is presented to the library in a soluble form at a concentration higher than the disassociation constant. Most commonly, the receptor bears a fluorescent tag. The beads bearing the ligand therefore bind fluorescent receptor, can be identified by their fluorescence under ultraviolet light, and can be separated manually or by a cell sorter. The number of beads that can be examined in this manner is theoretically infinite. However, even assuming automatic sorting of the beads (using a cell sorter) at a rate of 100 per second, a library of greater than $10^8$ compounds is not manageable, as it requires more than 10 days to sort through the beads. Presenting large numbers of beads to a receptor in high concentration also requires substantial amounts of receptor. Finally, artifacts associated with ligands covalently linked to a support are commonly encountered, where the receptor binds the supported ligand but not to the same ligand free in solution.

SUMMARY OF THE INVENTION

This invention provides a method for preparing molecules (ligands) that bind to a preselected receptor, whereby the receptor itself acts as an agent for either joining two ligand fragments to form a composite, tight binding ligand, or selects a composite ligand from a mixture in solution where ligand fragments are being joined and unjoined reversibly under equilibrium conditions. More specifically, it provides a method whereby a biological receptor is presented with a mixture, or library, of compounds that represent widely different types of structures, where each of these compounds bears one or more reactive groups that can form a covalent bond by reaction with a reactive group from another compound in the library, when two or more compounds are bound to the receptor at the same time. Alternatively, it provides a method whereby a biological receptor is presented with a mixture, or library, of compounds that represent widely different types of structures, where each of these compounds bears one or more reactive groups that can form a covalent bond in solution under reversible conditions by reaction with a reactive group from another compound in the library, where by binding to the product of the reaction, the receptor shifts the equilibrium in solution towards synthesis of the composite ligand with the tightest affinity for the receptor. In either case, the product of the receptor-assisted synthesis is isolated as a complex with the receptor, and then released and analyzed. This increases the power of combinatorial strategies by increasing the number of compounds that can be explored in a combinatorial experiment.

DETAILED DESCRIPTION OF THE INVENTION AND PREFERRED EMBODIMENTS

Consider a receptor R that binds to a ligand represented by the structure A-B. In general, both fragment A from the ligand and fragment B will individually bind to the receptor much more weakly than the ligand A-B itself. Often, however, the receptor R, when presented with A and B as a mixture, will bind these fragments synergistically to yield a complex R[A·B], where A and B are not joined covalently. This phenomenon is often exploited in biocatalysis. For example, in the inventor's laboratory, the enzyme nucleotidase will bind both a sugar phosphate derivative and a heterocycle synergistically and catalyze the hydrolysis of the phosphate linkage only when both fragments are bound (A. Moradian and S. A. Benner. *J. Am. Chem. Soc.* 114, 6980–6987 (1992)).

Consider next an arrangement where reactive groups x and y are appended to A and B respectively, to yield the fragments Ax and yB. Assume further than groups x and y can react reversibly with each other to yield the covalently joined molecule Ax'-y'B (a composite molecule), where the primes (') indicate that the reactive groups may have gained or lost atoms as a result of the reaction, and that the groups are correctly disposed in space in the R[Ax·yB] complex to react to give, in the complex, the complex R[Ax'-y'B] where the receptor holds the covalently joined composite molecule Ax'-y'B. Thermodynamic considerations show that the equilibrium constant for the reaction in the receptor binding pocket (R[Ax·yB]<->R[Ax'-y'B]) will be favored over the analogous reaction in solution (Ax·yB<->Ax'-y'B) by the same amount that favors intramolecular reactions over intermolecular interactions, and disfavored to the extent that the x'-y' linker is strained by the receptor binding interactions.

Consider now the analogous combinatorial system. In this case, a library of ligand fragments $A^c x$ are presented to the receptor with a library of ligand fragments $yB^c$. In this disclosure, the superscript "c" indicates that the unit is present in combinatorial form, and represents a mixture of compounds with different, independently varying structures. The system composed of the receptor and the two libraries is then allowed to approach equilibrium. The receptor will sample pairs of ligands by forming complexes $R[A^c x \cdot y B_c]$. In some cases, the x and y functional groups will be oriented correctly for a reaction to yield $R[A^c x'-y'B^c]$ where the two ligand fragments are covalently bound. In some case, the strain imposed by the covalent linkage will be such that the $A^c x'-y'B^c$ product fall off of the receptor, yielding under the reversible conditions of the reaction the two ligand fragments again $A^c x'$ and $y'B^c$. However, under some circumstances, the x'-y' bond in the $R[A^c x'-y'B^c]$ complex is not strained, allowing the full intramolecularity effect to be felt.

The discussion below is not affected if the receptor binds the composite ligand $A^c x'-y'B^c$ formed by reaction between Ax and yB in solution. Here, the receptor will remove the composite ligand with the greatest affinity from the pool of composite molecules being synthesized and degraded under equilibrium conditions. This will perturb the solution equilibrium in the direction of more synthesis of the composite ligand with the tightest affinity for the receptor.

In either case, thermodynamic considerations show that after equilibrium is attained, the receptor will have collected in its active site the tightest binding combination of $A^c x$ and $yB^c$.

This method, "receptor-assisted combinatorial synthesis", is useful because it permits the exploration of many more structures than a simple combinatorial experiment. With a library of a ligand fragments $A^c x$ and b ligand fragments $yB^c$, the total number of structures searched is a×b. That is, if a and b are numerically identical, the number of compounds searched is $a^2$ starting from a library containing only 2a compounds. Thus, while a combinatorial library set up in the classical sense can easily explore only up to $10^5$ to $10^6$ compounds, a receptor-assisted combinatorial experiment can explore these numbers of compounds squared, or $10^{10}$ to $10^{12}$ compounds.

Based on the analysis based on the immune system, this brings the scope of a combinatorial synthesis to a level where it is applicable for the discovery of lead compounds with useful disassociation constants (<1 μM).

The use of receptor assistance in combinatorial synthesis is quite general. A receptor assisted combinatorial experiment can be based on virtually any combinatorial library, built on virtually any scaffolding and incorporating virtually any structural diversity. The preferred libraries are those that contain between one hundred and one million compounds. In the most preferred embodiment of the present invention, libraries contain between one thousand and one hundred thousand different compounds.

Implementation of a receptor assisted combinatorial synthesis experiment requires three elements. First, procedures must be available to recover the receptor and the combinatorially synthesized ligand as a complex, and to remove ligand fragments that do not bind in combination to the receptor. The preferred method is to present the pair of libraries to the receptor in solution in an ultrafiltration apparatus (for example, an Amicon or Centricon ultrafiltration device) bearing a size-selective membrane that allows the ligand fragments to pass through, but that retains the receptor and receptor-ligand complex. In this implementation, the receptor and libraries are incubated until the system attains equilibrium. The mixture is then passed through the ultrafilter. The receptor holding the most tightly bound $A^c x'-y'B^c$ composite ligands is retained on the surface of the membrane, and the receptor and the bound molecules are recovered from the membrane. The ligand is then recovered and analyzed.

For the best results, the preferred concentration of each component of the library is one to ten times the concentration of the receptor [R]. This ensures that there will be enough of the tightest bound composite ligand to saturate the receptor. The preferred concentration of the receptor is one to ten times the disassociation constant of the most tightly binding $A^c x'-y'B^c$ product from the receptor. This ensures that the tightest binding ligand composite will be effectively removed from solution. The concentration of the receptor and the volume of the reactor must be chosen so that the total number of moles of receptor (corresponding to the maximum number of moles of $A^c x'-y'B^c$ product that might be recovered from the receptor-assisted combinatorial reaction) is greater than the amount required by the analytical method used to assign the structure to the $A^c x'-y'B^c$ product. In the most preferred embodiment of the present invention, the concentration of the receptor is from 0.1 to 1.0 μM, the volume of the reactor is 10 mL, the total library concentration is from 50 to 200 mM, and the diversity of the library with each ligand fragment is between ten thousand and one million.

Second, a method for the analysis of the $A^c x'\text{-}y'B^c$ product must be in hand. The preferred method is to extract the $A^c x'\text{-}y'B^c$ product from the receptor, to determine the molecular mass of the product by mass spectroscopy, and to subject the $A^c x'\text{-}y'B^c$ product to degradation, and to analyze the degradation products. The simplest degradation involves the cleavage of the x'-y' bond to yield two fragments whose molecular masses are determined by mass spectroscopy. The ligand fragments can then be analyzed further using methods standard in the art for the component fragments.

Third, the reactive groups x and y must be chosen to facilitate a receptor assisted combinatorial synthesis. The reaction between x and y must be reversible in solution; otherwise the full $\alpha^2$ set of combinatorial molecules will be prepared irreversibly in situ before the receptor can select from the pool the best binding pair. Two preferred embodiments of the invention involve the reaction of amino groups with aldehyde groups to form imines, and the reaction of thiol groups with aldehyde groups to form thioherniacetals. The first embodiment has the advantage of allowing the conversion of the hydrolyzable imine linkage into the stable amine linkage via treatment with sodium borohydride.

The most preferred embodiment has the reactive groups x and y identical, permitting the combinatorial libraries $A^c x$ and $yB^c$ to be identical as well. In this embodiment, both x and y are thiol groups, and the linker joining them is a disulfide bond. The reaction is rendered reversible by the presence of a redox buffer (for example, mercaptoethanol and its oxidized (disulfide) dimer, or the library itself in the presence of oxygen, at pH 8–9).

However, virtually any reaction where the equilibrium constant $[A^c x][yB^c]/[A^c x'\text{-}y'B^c]$ in solution is between 1 M and $10^{-9}$ M, and the rate constant for the joining reaction is between 1 and $10^7$ $M^{-1}sec^{-1}$ (more preferably between $10^4$ and $10^7$ $M^{-1}sec^{-1}$) is useful for the receptor-assisted combinatorial synthesis.

Further, it is possible to expand the receptor-assisted combinatorial synthesis strategy to yield composite ligands built from more than two components of the library. For example, libraries of the type $R^c$-SH incubated with libraries of the type HS-$Q^c$-SH will yield composite ligands build from three fragments, with the general formula $R^c$-SS-$Q^c$-SS-$R^c$. One preferred embodiment of this type, employing joining chemistry with equilibrium constant in solution between $10^{-3}$ M and $10^{-6}$ M, involves the borate-based assembly of 1,2-diols (Example 5). These diols form cyclic borate esters; a single boron will organize two 1,2-diols to yield a spiro structure with boron a the central atom.

As will be appreciated by one skilled in the art, the receptor-assisted combinatorial synthesis strategy can be expanded to join more than three fragments. This has the advantage of allowing smaller libraries to achieve the same composite degeneracy.

EXAMPLE 1

Receptor Assisted Combinatorial Experiment with Disulfide Chemistry

A pool of peptides is prepared by automated solid phase synthesis, with each peptide having the general sequence:

H$_2$N—Xxx-Xxx-Yyy-Xxx-Cys—COOH Seq. ID 1.

where Xxx represents a standard amino acid (except cysteine), and where Yyy represents a 1:1 mixture of phosphotyrosine and the mixture of standard amino acids (except cysteine) presented in combinatorial form. The peptide mixture (total concentration 100 mM) containing ca. 130000 compounds is mixed with the Hck Src homology 2 domain (1 $\mu$M) in a 10 mL ultrafiltration tube containing Tris buffer (100 mM, pH 8.5) and mercaptoethanol (10 mM) in the presence of oxygen. The predominant products are the disulfide-linked peptides with the general formula:

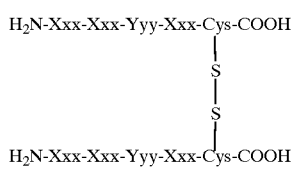

The tightest binding product is recovered by passing the mixture through an ultrafiltration membrane, which retains the Src homology 2 domain bound to the tightest binding disulfide peptide. The filter is then washed with dilute (100 mM) acetic acid, and the disulfide linked peptide is eluted from the receptor and recovered in the eluate passing through the filter. The structure of the ligand is analyzed first by mass spectrometry to obtain a parent peak, and by tandem mass spectrometry to obtain fragment peaks. The material is then oxidized with performic acid, and the fragments are separated by HPLC. Finally the two product fragments thus obtained are identified by sequencing by Edman degradation.

EXAMPLE 2

Receptor Assisted Combinatorial Experiment with a Biased Library

A pool of peptides is prepared by automated solid phase synthesis, with each peptide having the general sequence:

H$_2$N—Cys-Xxx-Xxx-Xxx-Xxx-Xxx-Cys—COOH Seq. ID 2.

where Xxx represents a standard amino acid (except cysteine) presented in combinatorial form, with proline representing 30% of the total amino acid at each position and the remaining 18 standard amino acids contributing equally to the remaining 70% mixture. The peptide mixture (total concentration 100 mM) containing ca. 500000 compounds is mixed with the PI-3K Src homology 3 domain (1 $\mu$M) in a 10 mL ultrafiltration tube containing Tris buffer (100 mM, pH 8.5) and mercaptoethanol (10 mM) in the presence of oxygen. The predominant product is the cyclic dipeptide joined by two disulfide links. The tightest binding product is recovered as a complex with the Src homology 3 domain by passing the mixture through an ultrafiltration membrane. The receptor-ligand complex on the membrane is then eluted from the Src homology 3 domain by washing the filter with dilute (100 mM) acetic acid, and the disulfide-linked peptide is recovered in the eluate passing through the filter. The structure of the ligand is analyzed first by mass spectrometry to obtain a parent peak, and by tandem mass spectrometry to obtain fragment peaks. The material is then oxidized with performic acid, and the fragments are analyzed by mass spectrometry. The fragments are then separated by HPLC and sequenced by Edman degradation.

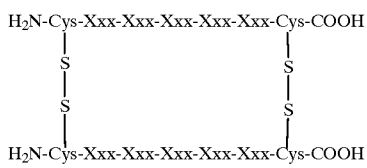

EXAMPLE 3
Receptor Assisted Combinatorial Experiment with an Imine Linkage

Two separate peptide libraries are prepared by solid phase methods. The first library is built from polypeptides that are terminated at the amino end by an alpha-ketoacid derived from the standard alpha-amino acids ($R^c$=H—, $CH_3$—, $(CH_3)_2CH$—, $(CH_3)_2CH_2$—, Ph—$CH_2$—, HO—Ph—$CH_2$—, $H_2NCOCH_2$—, $H_2NCOCH_2CH_2$—, MeS$CH_2CH_2$—, HO$CH_2$—). Members of the library have the general sequence:

$R^c$—CO—CONH—Xxx-Xxx-Xxx-Xxx—COOH Seq. ID 3.

where Xxx represents a standard amino acid (except cysteine) presented in combinatorial form.

The second library is built from polypeptides that have the general sequence:

$Cl_3CCH_2$—OCONH—Xxx-Xxx-Xxx-pY-Glu—NH—$(CH_2)_2$—NH2 Seq. ID 4.

where Xxx represents a standard amino acid (except cysteine) presented in combinatorial form, and pY is phosphotyrosine. This is prepared by standard solid phase synthesis on solid support followed by incubation with ethylenediamine.

The two peptide libraries (total concentration 100 mM each) are incubated with the Hck Src homology 2 domain (1 $\mu$M) in a 10 mL ultrafiltration tube containing borate buffer (100 mM, pH 8.5) and mercaptoethanol (10 mM) in the presence of oxygen to obtain composite products with the general formula $Cl_3CCH_2$—OCONH—Xxx-Xxx-Xxx-pY-Glu—NH—$(CH_2)_2$—N=C($R^c$)—CONH—Xxx-Xxx-Xxx-Xxx—COOH. The tightest binding composite product is recovered as a complex with the receptor by ultrafiltration as before. The filter is then washed with dilute (100 mM) acetic acid, and the ligand is eluted from the receptor and recovered in the eluate passing through the filter. The structure of the ligand is analyzed first by mass spectrometry to obtain a parent peak, and by tandem mass spectrometry to obtain fragment peaks. The recovered composite ligand is then fragmented with semicarbazide, and the fragments analyzed by mass spectrometry. The recovered composite ligand is also reduced with sodium borohydride, and sequenced by Edman degradation, which degrades the ligand from the internal secondary amine. The peptide is then treated with alkaline phosphatase to remove the phosphate group from tyrosine, the amino terminal protecting groups removed, and the remainder of the sequence determined by Edman degradation.

In this case, it should be noted that the receptor assisted combinatorial experiment can also yield composite ligands built from three or more members of the library.

EXAMPLE 4
Receptor Assisted Combinatorial Experiment with a Non-peptidic Library 3-Mercaptopropyltrimethoxysilane (Aldrich) is reacted with a combinatorial pool of 60 primary ($R^c$—$CH_2$—OH) and secondary ($R^cR^cCH$—OH) alcohols ($R^c$=H—, $CH_3$—, $(CH_3)_2CH_2$—, Ph—$CH_2$—, HO—Ph—$CH_2$—, $H_2NCOCH_2$—, $H_2NCOCH_2CH_2$—, $CF_3CONHCH_2CH_2CH_2$—, and MeOOC$CH_2CH_2$—). This yields a set of ca. 250000 combinatorial molecules with the general formula HS$CH_2CH_2CH_2$Si(O$R^c$)$_3$. The library is incubated in a total concentration of 100 mM with beta-lactamase (1 $\mu$M) in a 10 mL ultrafiltration tube containing Tris buffer (100 mM, pH 8.5) in the presence of oxygen to obtain composite products of the general formula ($R^c$O)$_3$SiCH$_2$CH$_2$CH$_2$SSCH$_2$CH$_2$CH$_2$Si(O$R^c$)$_3$. The tightest binding composite ligand is recovered as a complex by ultrafiltration, and eluted from the receptor washing the filter with acetic acid (100 mM). The structure of the ligand is analyzed by mass spectrometry to obtain a parent ion, and by tandem mass spectrometry to obtain fragments. The ligand is then reduced to give product fragments with the general formula HS$CH_2CH_2CH_2$Si(O$R^c$)$_3$. The structures of these are analyzed by mass spectrometry and by tandem mass spectrometry. These are then treated with fluoride, and the structures of the alcohols released are determined by mass spectrometry.

EXAMPLE 5
Receptor Assisted Combinatorial Experiment with Cyclic Borates

A library of carbonyl compounds ($R^cR^cCO$) is obtained, where $R^c$=—H, —$CH_3$, —$CH_2CH_2CH(CH_3)_2$, —$CH_2$Ph, —COO—, and CONH$_2$. This is reacted with SmI$_2$ to give a library of 1,2 diols (Molander, G. A., Chem. Rev. 92, 29–68 (1992)). The reaction mixture is passed through a column bearing a semicarbazide (RNHCONHNH$_2$) to remove any unreacted ketone starting materials; the diols pass through the column. The library (total concentration 100 mM) is incubated with beta lactamase (1 $\mu$M) in a 10 mL ultrafiltration tube containing sodium borate buffer (100 mM, pH 8.5). The predominant composite products are orthoborate esters formed by complexation of two diols, in equilibrium with borate esterified with one diol (Coddington, J. M., Taylor, M. J. J. Coord. Chem. 20, 27–38 (1989)). The tightest binding product is recovered as a complex by ultrafiltration. The filter is then washed with dilute (10 mM) acetic acid. The two diols are recovered in the washings that pass through the filter, and their molecular masses are determined by mass spectrometry. The diols are then cleaved with periodate to yield two ketones, whose masses are determined by mass spectrometry.

EXAMPLE 6
Receptor Assisted Combinatorial Experiment with Oligo-nucleotide Analogs A library of oligonucleotide analogs, as disclosed in U.S. Pat. No. 5,216,141 (Oligonucleotide Analogs Containing Sulfur Linkages) containing six units, with the general formula:

HS—Nnn-So$_2$-Nnn-So$_2$-Nnn-So$_2$-Nnn-So$_2$-Nnn-So$_2$-Nnn—OH where Nnn represents a nucleoside analog building block bearing one of the four standard bases (adenine, guanine, cytosine, and thymine) is presented as a library (total concentration 100 mM) to HIV-1 reverse transcriptase (1 $\mu$M) in a 10 mL ultrafiltration tube containing borate buffer (100 mM, pH 8.5) and mercaptoethanol (10 mM) in the presence of oxygen to obtain composite products joined by a disulfide bond. These are recovered as above by ultrafiltration, and the composite ligand anralyzed by mass spectrometry, reduced, and the fragments analyzed by mass spectrometry.

EXAMPLE 7

Receptor Assisted Combinatorial Experiment with a Thiohemiacetal Linikage

Two separate peptide libraries are prepared by solid phase methods. The first library is built from polypeptides that are termiinated at the amino end by an alpha-ketoacid derived from the standard alpha-amino acids ($R^c$=H—, $CH_3$—, $(CH_3)_2CH$—, $(CH_3)_2CH_2$—, $Ph$—$CH_2$—, $HO$—$Ph$—$CH_2$—, $H_2NCOCH_2$—, $H_2NCOCH_2CH_2$—, $MeSCH_2CH_2$—, $HOCH_2$—). Members of the library have the general sequence:

$R^c$—CO—CONH—Xxx-Xxx-Xxx-Xxx—COOH Seq. ID 3 where Xxx represents a standard amino acid (except cysteine) presented in combinatorial form.

The second library is built from polypeptides that have the general sequence:

$H_2N$—Xxx-Xxx-Xxx-pY-Glu—NH—$(CH_2)_2$—SH Seq. ID 5 where Xxx represents a standard amino acid (except cysteine) presented in combinatorial form, and pY is phosphotyrosine.

The two peptide libraries (total concentration 100 mM each) are incubated with the Hck Src homology 2 domain (1 $\mu$M) in a 10 mL ultrafiltration tube containing borate buffer (100 mM, pH 8.5) and mercaptoethanol (10 mM) in the presence of oxygen to obtain composite products with the general formula $H_2N$—Xxx-Xxx-Xxx-pY-Glu—NH—$(CH_2)_2$—S—C(OH)($R^c$)—CONH—Xxx-Xxx-Xxx-Xxx—COOH. The tightest binding composite product is recovered as a complex with the receptor by ultrafiltration as before. The filter is then washed with dilute (100 mM) acetic acid, and the ligand is eluted from the receptor and recovered in the eluate passing through the filter. The structure of the ligand is analyzed first by mass spectrometry to obtain a parent peak, and by tandem mass spectrometry to obtain fragment peaks. The recovered composite ligand is then fragmented with semicarbazide, and the fragments analyzed by mass spectrometry and by Edman degradation, following treatment with alkaline phosphatase to remove the phosphate group from tyrosine. The ketoacid at the terminal end of the second fragment is then cleaved with periodate, and the products sequenced by Edman degradation.

EXAMPLE 8

Receptor Assisted Combinatorial Experiment Joining More than Two Members of a Library via Disulfide Bonds.

The library of molecules with the general formula $HSCH_2CH_2CH_2Si(OR^c)_3$ from Example 4 is incubated with beta-lactamase as in Example 4 together with a library of molecules with the general formula HS—$CHQ^c$—$CHQ^c$—SH ($Q^c$=H—, $CH_3$—, $(CH_3)_2CH$—, $(CH_3)_2CH_2$—, $Ph$—$CH_2$—, $HO$—$Ph$—$CH_2$—, $H_2NCOCH_2$—, $H_2NCOCH_2CH_2$—, $MeSCH_2CH_2$—, $HOCH_2$—) under conditions described in Example 4. The composite products obtained, with the general formula:

$(R^cO)_3SiCH_2CH_2CH_2SS$—$CHQ^c$—$CHQ^c$—$SSCH_2CH_2CH_2Si(OR^c)_3$.

are isolated and analyzed as in Example 4.

What is claimed is:

1. A method for preparing a ligand for a preselected receptor that consists of mixing a receptor R with two mixtures of compounds $A^c x$ and $yB^c$, wherein x and y are functional groups that undergo a reversible reaction with each other to form at least one covalent bond x'-y' to yield composite molecules with the general formula $A^c x'$-$y'B^c$, where complexation of the receptor to the product with the tightest affinity for the receptor shifts the equilibrium distribution to favor the synthesis of the composite ligand $A^c x'$-$y'B^c$ with the greatest affinity for the receptor, wherein said functional groups are selected from the group consisting of thiol, amino ketone and aldehyde.

2. The method of claim 1 wherein said covalent bond is selected from the group consisting of S—S, N=C, and S—C(OH).

3. A method for preparing a ligand for a preselected receptor that consists of mixing a receptor R with two mixtures of compounds $A^c x$ and $yB^c$, wherein x and y are functional groups that undergo a reversible reaction with a third species Z to form at least two covalent bonds yielding molecules with the general formula $A^c x'$-$Z'$-$y'B^c$, where complexation of the receptor to the ligand of this form with the tightest affinity for the receptor shifts the equilibrium distribution to favor the synthesis of the combination of $A^c x$ and $yB^c$ with the tightest affinity for the receptor, wherein said species Z is a borate.

4. A method for preparing a ligand for a preselected receptor that consists of mixing a receptor R with two mixtures of compounds $A^c$ x and $yB^c$ wherein x and y are functional groups that undergo a reversible reaction with a third species Z to form at least two covalent bonds yielding molecules with the general formula $A^c x'$-$Z'$-$y'$-$B^c$, where complexation of the receptor to the ligand of the form with the tightest affinity for the receptor shifts the equilibrium distribution to favor the synthesis of the combination of $A^c x$ and $yB^c$ with the tightest affinity for the receptor, wherein said functional groups are selected from the group consisting of thiol, amino, ketone and aldehyde.

5. The method of claim 4 wherein said covalent bonds are selected from the group consisting of S—S, N=C, and S—C(OH).

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 5 amino acids
      (B) TYPE: amino acid
      (D) TOPOLOGY: linear (ii) MOLECULE TYPE: amino acid (vi) ORIGINAL SOURCE: synthetic (ix) FEATURE:
      (D) OTHER INFORMATION: The formula represents a library, not a
         sequence, not conforming to controlled vocabulary in 37
         CFR. Xaa is a degenerate position. The 3rd amino acid
         is phosphotyrosine.

(xi) SEQUENCE DESCRIPTION: SEQ ID NO:1:

Xaa Xaa Xaa Xaa Cys
               5

(2) INFORMATION FOR SEQ ID NO:2:

(i) SEQUENCE CHARACTERISTICS:
      (A) LENGTH: 7 amino acids
      (B) TYPE: amino acid
      (D) TOPOLOGY: linear (ii) MOLECULE TYPE: amino acid (vi) ORIGINAL SOURCE: synthetic

```
        (ix) FEATURE:
              (D) OTHER INFORMATION: The formula represents a library, not a
                    sequence, not conforming to controlled vocabulary in 37
                    CFR. Xaa is a degenerate position.

(xi) SEQUENCE DESCRIPTION: SEQ ID NO:2:

Cys Xaa Xaa Xaa Xaa Xaa Cys
                  5

(2) INFORMATION FOR SEQ ID NO:3:

(i) SEQUENCE CHARACTERISTICS:
              (A) LENGTH: 4 amino acids
              (B) TYPE: amino acid
              (D) TOPOLOGY: linear (ii) MOLECULE TYPE: amino acid (vi) ORIGINAL SOURCE: synthetic (ix) FEATURE:
              (D) OTHER INFORMATION: The formula represents a library, not a
                    sequence, not conforming to controlled vocabulary in 37
                    CFR. Xaa is a degenerate position. Important features of
                    the library compounds are not captured by the description.

(xi) SEQUENCE DESCRIPTION: SEQ ID NO:3:

Xaa Xaa Xaa Xaa (2) INFORMATION FOR SEQ ID NO:4:

(i) SEQUENCE CHARACTERISTICS:
              (A) LENGTH: 5 amino acids
              (B) TYPE: amino acid
              (D) TOPOLOGY: linear (ii) MOLECULE TYPE: amino acid (vi) ORIGINAL SOURCE: synthetic (ix) FEATURE:
              (D) OTHER INFORMATION: The formula represents a library, not a
                    sequence, not conforming to controlled vocabulary in 37
                    CFR. Xaa is a degenerate position. Important features of
                    the library compounds are not captured by the
                    description. 4th amino acid is phosphotyrosine.

(xi) SEQUENCE DESCRIPTION: SEQ ID NO:4:

Xaa Xaa Xaa Xaa Glu
                  5

(2) INFORMATION FOR SEQ ID NO:5:

(i) SEQUENCE CHARACTERISTICS:
              (A) LENGTH: 5 amino acids
              (B) TYPE: amino acid
              (D) TOPOLOGY: linear (ii) MOLECULE TYPE: amino acid (vi) ORIGINAL SOURCE: synthetic (ix) FEATURE:
              (D) OTHER INFORMATION: The formula represents a library, not a
                    sequence, not conforming to controlled vocabulary in 37
                    CFR. Xaa is a degenerate position. Important features of
                    the library compounds are not captured by the
                    description. 4th amino acid is phosphotyrosine.

(xi) SEQUENCE DESCRIPTION: SEQ ID NO:5:

Xaa Xaa Xaa Xaa Glu
```